United States Patent
Bewley, Jr.

(10) Patent No.: US 8,834,646 B2
(45) Date of Patent: Sep. 16, 2014

(54) TURBIDITY SENSOR AND RELATED CONSUMER APPLIANCE

(75) Inventor: Wilbur Carl Bewley, Jr., Nicholasville, KY (US)

(73) Assignee: General Electric Company, Schenectady, NY (US)

( * ) Notice: Subject to any disclaimer, the term of this patent is extended or adjusted under 35 U.S.C. 154(b) by 440 days.

(21) Appl. No.: 13/108,271

(22) Filed: May 16, 2011

(65) Prior Publication Data

US 2012/0090654 A1 Apr. 19, 2012

(51) Int. Cl.
*A47L 15/42* (2006.01)
*G01N 21/49* (2006.01)
*G01N 21/53* (2006.01)
*D06F 39/00* (2006.01)
*G01N 21/27* (2006.01)

(52) U.S. Cl.
CPC ........... *A47L 15/4297* (2013.01); *G01N 21/274* (2013.01); *G01N 21/534* (2013.01); *G06F 2202/02* (2013.01); *A47L 2401/10* (2013.01); *D06F 39/004* (2013.01)
USPC ....................................................... 134/56 D

(58) Field of Classification Search
USPC ....................................................... 134/56 D
See application file for complete search history.

(56) References Cited

U.S. PATENT DOCUMENTS

| | | | | |
|---|---|---|---|---|
| 4,257,708 A | * | 3/1981 | Fukuda | 356/435 |
| 5,291,626 A | * | 3/1994 | Molnar et al. | 8/158 |
| 5,555,583 A | * | 9/1996 | Berkcan | 8/158 |
| 5,560,060 A | | 10/1996 | Dausch et al. | |
| 5,589,935 A | * | 12/1996 | Biard | 356/339 |
| 5,889,192 A | | 3/1999 | Engel | |

* cited by examiner

*Primary Examiner* — Michael Barr
*Assistant Examiner* — Jason Riggleman
(74) *Attorney, Agent, or Firm* — Dority & Manning, P.A.

(57) ABSTRACT

A turbidity sensor includes a housing having a first side along an exterior surface defining a channel for holding a liquid, the housing also having a second side along an interior surface; a first turbidity sensor having an emitter and a receiver adjacent the channel; and a second turbidity sensor having an emitter and a receiver substantially identical to that of the first turbidity sensor located on the second side of the housing spaced from the channel. The liquid is precluded from passing between the emitter and the receiver of the second turbidity sensor at any time. The first turbidity sensor outputs a signal combinable with the signal from the second turbidity sensor to determine the turbidity of the liquid while accounting for the temperature of the liquid without determining the temperature of the liquid. Related dishwasher designs include such sensors.

10 Claims, 4 Drawing Sheets

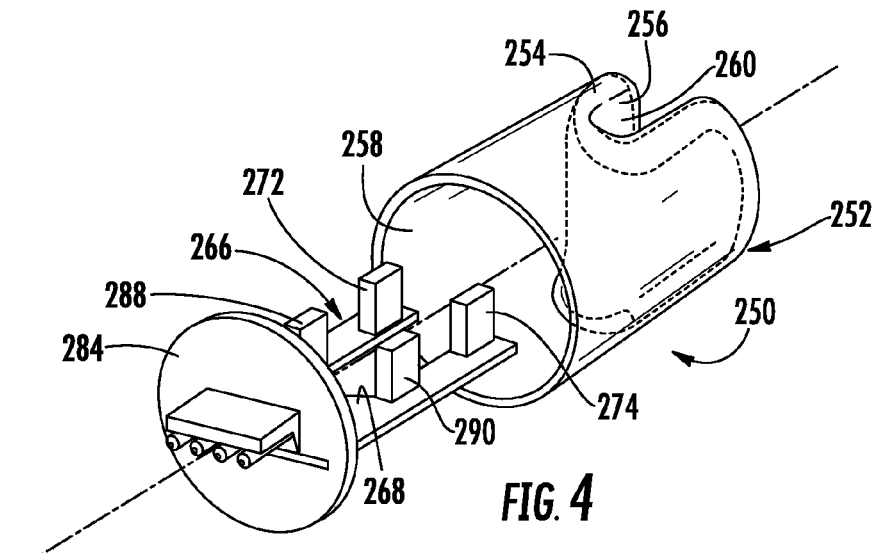
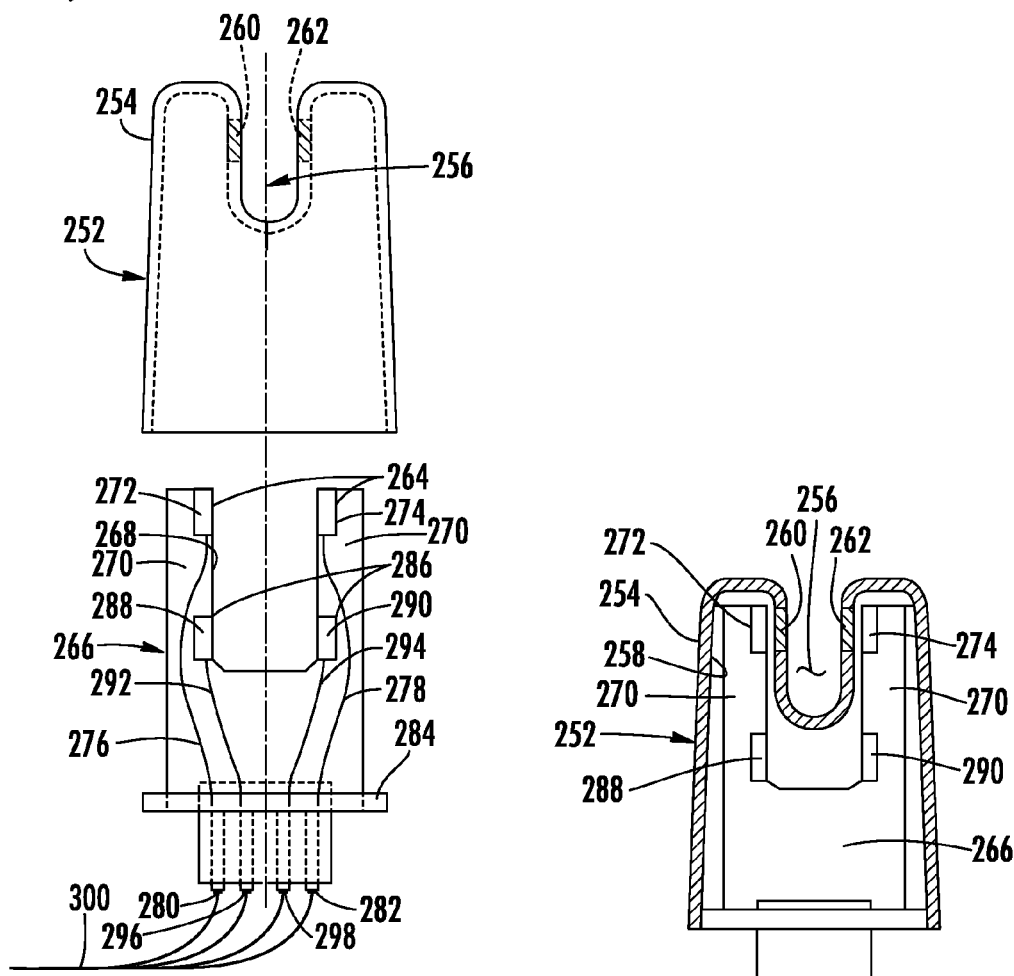
FIG. 4
FIG. 5
FIG. 6

TURBIDITY SENSOR AND RELATED CONSUMER APPLIANCE

FIELD OF THE INVENTION

The present disclosure relates generally to turbidity sensors that can be used in a consumer appliance such as a dishwasher.

BACKGROUND OF THE INVENTION

Consumer appliances such as dishwashers of various types have been proposed wherein items are placed in a wash chamber which is filled and emptied according to desired wash sequences. Recently, dishwasher manufacturers have focused even more on efficiency in implementing new designs. Thus, an amount of electricity, an amount of detergent, and an amount of water used are all monitored in an attempt to provide efficient and environmentally sensitive machines.

One approach for improving efficiency has been using feedback as to measured qualities of the water being used in a given cycle. For example, turbidity of water being cycled through as dishwasher can be measured and used to optimize the cycle to only use as much water as is needed to clean a given load. The amount of water could vary, in some cases, depending on the type of items being washed, the amount of items being washed, and the cleanliness of the items being washed before the wash cycle starts. In some cases, for example, people will rinse off dishes in a sink before placing them in a dishwasher. Doing so can reduce the need for pre-washing to remove debris.

U.S. Pat. Nos. 5,555,583 and 5,560,060, owned by Applicants' Assignee, and incorporated by reference herein, both disclose use of such turbidity measurements to improve cycle efficiency. The methods disclosed in the patents also use water temperature information to help fine tune the measurements, since turbidity readings often vary with temperature. While the devices and methods disclosed therein work well for their intended applications, efficiency improvements are always welcome.

Accordingly, other designs for turbidity sensing devices and related consumer appliances and dishwashers including those addressing one or more drawbacks of conventional devices and dishwashers would be welcome.

BRIEF DESCRIPTION OF THE INVENTION

Aspects and advantages of the invention will be set forth in part in the following description, or may be obvious from the description, or may be learned through practice of the invention.

According to certain aspects of the present disclosure, a sensor for measuring a turbidity of a liquid includes a housing having a first side defining a channel for holding the liquid, the housing also having a second side opposite the first side. A first turbidity sensor has an emitter and a receiver, the emitter and receiver being located on the second side of the housing adjacent the channel so that the liquid can be present between the emitter and the receiver of the first turbidity sensor, the first turbidity sensor outputting a signal. A second turbidity sensor has an emitter and a receiver substantially identical to that of the first turbidity sensor, the emitter and receiver being located on the second side of the housing spaced from the channel so that air and not the liquid is present between the emitter and the receiver of the second turbidity sensor, the second turbidity sensor outputting a signal. The signal from the first turbidity sensor is combinable with the signal from the second turbidity sensor to determine the turbidity of the liquid without determining the temperature of the liquid. Various options and modifications are possible.

According to certain other aspects of the disclosure, a consumer appliance for washing objects includes a cabinet holding wash elements that transition through a wash cycle to wash the objects; a liquid flow path through the cabinet used for washing the objects, the flow path defined in part by a housing having a first side defining a channel for holding the liquid, the housing also having a second side opposite the first side; a controller in the cabinet for controlling the water cycle and the wash elements; and a sensor in the cabinet for measuring a turbidity of the liquid. The sensor includes a first turbidity sensor having an emitter and a receiver, the emitter and receiver being located on the second side of the housing adjacent the channel so that the liquid can be present between the emitter and the receiver of the first turbidity sensor, the first turbidity sensor outputting a signal to the controller. The sensor also includes a second turbidity sensor having an emitter and a receiver substantially identical to that of the first turbidity sensor, the emitter and receiver being located on the second side of the housing spaced from the channel so that air and not the liquid is present between the emitter and the receiver of the second turbidity sensor, the second turbidity sensor outputting a signal to the controller. The signal from the first turbidity sensor being combinable with the signal from the second turbidity sensor by the controller to determine the turbidity of the liquid without determining the temperature of the liquid. Again, various options and modifications are possible.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 4 provides an exploded perspective view of a sensor according to certain aspects of the disclosure;

FIG. 5 provides an exploded top view of the sensor of FIG. 4; and

FIG. 6 provides a sectional view of the sensor of FIG. 4 showing locations of first and second turbidity sensors.

DETAILED DESCRIPTION OF THE INVENTION

Figure 1:
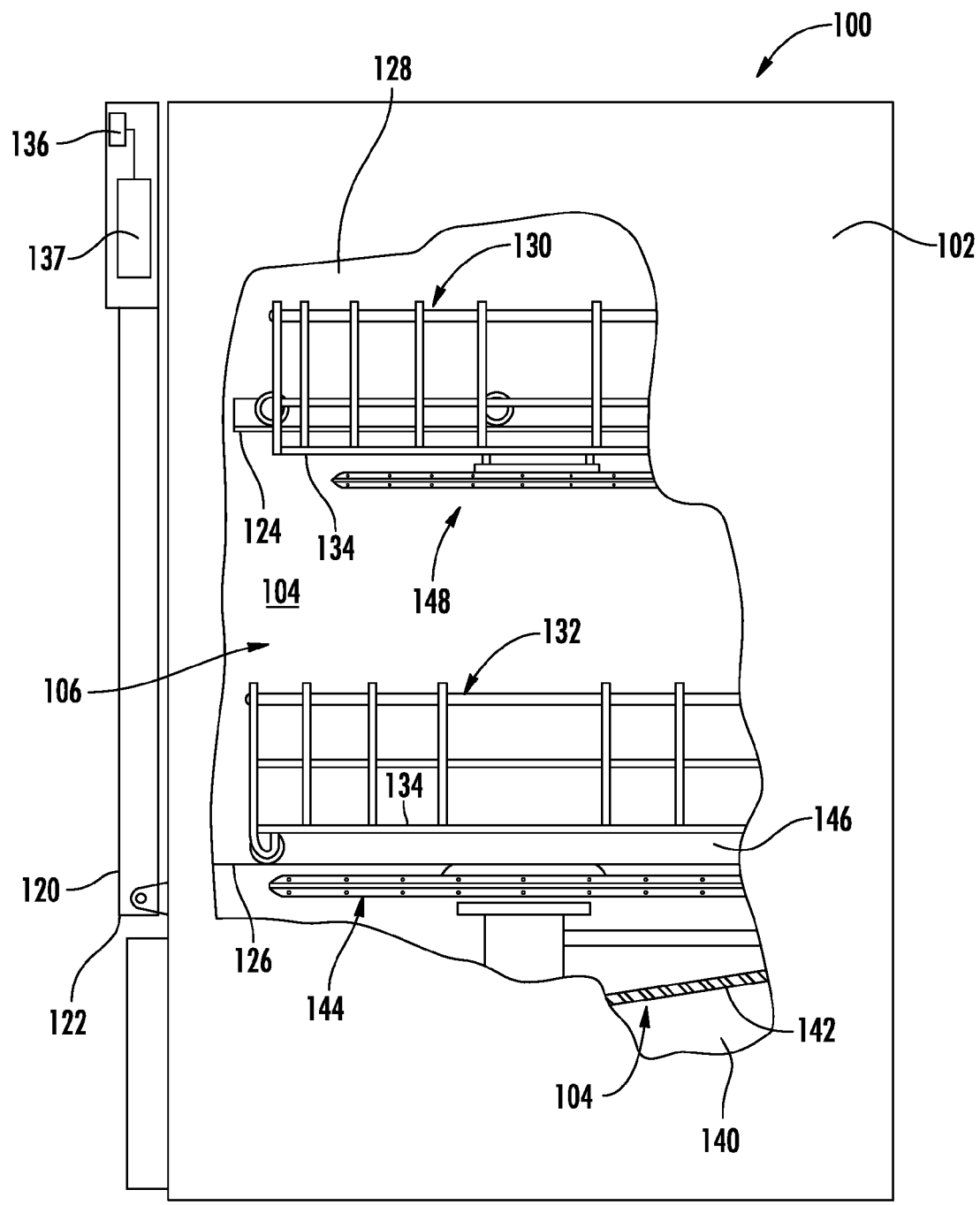
FIG. 1 provides a side partial cut-away view of an exemplary dishwasher that may be configured in accordance with aspects of the invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As discussed in greater detail below, embodiments of the present disclosure relate to a sensing device that can be used with a consumer appliance such as a dishwasher, washing machine, or the like. FIG. 1 depicts an exemplary domestic dishwasher 100 that may be configured in accordance with aspects of the disclosure, although it should be understood that the sensor disclosed herein is not limited to use with consumer appliances or dishwashers or washing machines per se.

For the particular embodiment of FIG. 1, the dishwasher 100 includes a cabinet 102 having a tub 104 therein that defines a wash chamber 106. The tub 104 includes a front opening (not shown in FIG. 1) and a door 120 hinged at its bottom 122 for movement between a normally closed vertical position (shown in FIG. 1) wherein the wash chamber 106 is sealed shut for washing operation, and a horizontal open position for loading and unloading of articles from the dishwasher. Upper and lower guide rails 124, 126 are mounted on tub side walls 128 and accommodate upper and lower roller-equipped racks 130, 132, respectively. Each of the upper and lower racks 130, 132 is fabricated into lattice structures including a plurality of elongate members 134, and each rack 130, 132 is adapted for movement between an extended loading position (not shown) in which the rack is substantially positioned outside the wash chamber 106, and a retracted position (shown in FIG. 1) in which the rack is located inside the wash chamber 106. A silverware basket (not shown) may be removably attached to the lower rack 132 for placement of silverware, utensils, and the like, that are too small to be accommodated by the upper and lower racks 130, 132.

The dishwasher 100 further includes a lower spray-arm-assembly 144 that is rotatably mounted within a lower region 146 of the wash chamber 106 and above a tub sump portion 142 so as to rotate in relatively close proximity to the lower rack 132. A mid-level spray-arm assembly 148 is located in an upper region of the wash chamber 106 and may be located in close proximity to upper rack 130. Additionally, an upper spray arm assembly (not shown) may be located above the upper rack 130.

The lower and mid-level spray-arm assemblies 144, 148 and the upper spray arm assembly are fed by a fluid circulation assembly for circulating water and dishwasher fluid in the tub 104. The fluid circulation assembly may be located in a machinery compartment 140 located below the bottom sump portion 142 of the tub 104, as generally recognized in the art. Each spray-arm assembly includes an arrangement of discharge ports or orifices for directing washing liquid onto dishes or other articles located in the upper and lower racks 130, 132, respectively. The arrangement of the discharge ports in at least the lower spray-arm assembly 144 provides a rotational force by virtue of washing fluid flowing through the discharge ports. The resultant rotation of the lower spray-arm assembly 144 provides coverage of dishes and other dishwasher contents with a washing spray.

The dishwasher 100 is further equipped with a controller 137 to regulate operation of the dishwasher 100. The controller may include a memory and microprocessor, CPU or the like, such as a general or special purpose microprocessor operable to execute programming instructions or micro-control code associated with a cleaning cycle. The memory may represent random access memory such as DRAM, or read only memory such as ROM or FLASH. In one embodiment, the processor executes programming instructions stored in memory. The memory may be a separate component from the processor or may be included onboard within the processor.

The controller 137 may be positioned in a variety of locations throughout dishwasher 100. In the illustrated embodiment, the controller 137 may be located within a control panel area of door 120 as shown. In such an embodiment, input/output ("I/O") signals may be routed between the control system and various operational components of dishwasher 100 such as the turbidity sensor along wiring harnesses that may be routed through the bottom 122 of door 120. Typically, the controller 137 includes a user interface panel 136 through which a user may select various operational features and modes and monitor progress of the dishwasher 100. In one embodiment, the user interface 136 may represent a general purpose I/O ("GPIO") device or functional block. In one embodiment, the user interface 136 may include input components, such as one or more of a variety of electrical, mechanical or electro-mechanical input devices including rotary dials, push buttons, and touch pads. The user interface 136 may include a display component, such as a digital or analog display device designed to provide operational feedback to a user. The user interface 136 may be in communication with the controller 137 via one or more signal lines or shared communication busses.

It should be appreciated that the invention is not limited to any particular style, model, or other configuration of dishwasher, and that the embodiment depicted in FIG. 1 is for illustrative purposes only. For example, instead of the racks 130, 132 depicted in FIG. 1, the dishwasher 100 may be of a known configuration that utilizes drawers that pull out from the cabinet and are accessible from the top for loading and unloading of articles.

Figure 2:
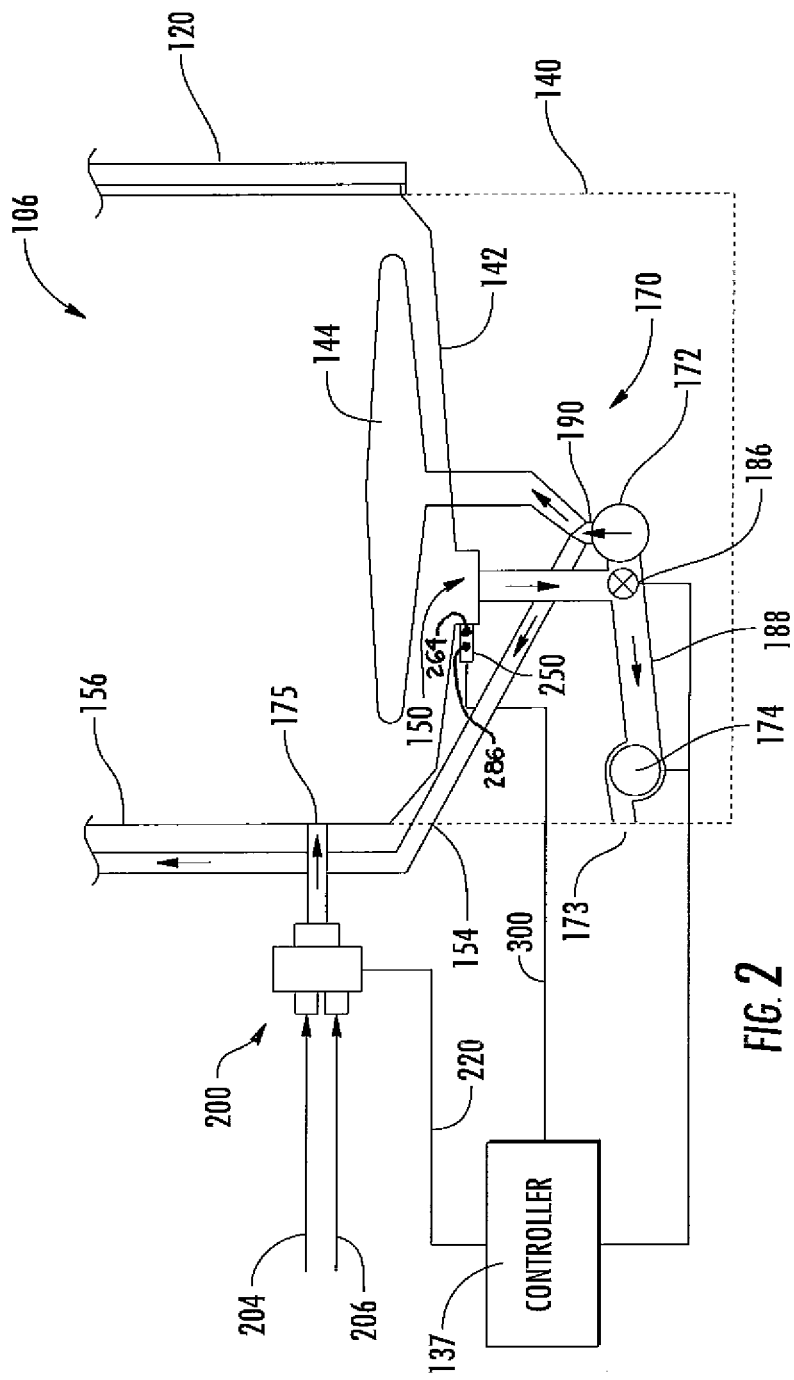
FIG. 2 is a schematic view of one possible fluid system the dishwasher of FIG. 1.

FIG. 2 schematically illustrates an embodiment of a fluid circulation assembly 170 configured below the wash chamber 106. Although one embodiment of a fluid circulation assembly that is operable to perform in accordance with aspects of the disclosure is shown, it is contemplated that other fluid circulation assembly configurations may similarly be utilized without departing from the spirit and scope of the invention. The fluid circulation assembly 170 includes a circulation pump assembly 172 and a drain pump assembly 174, both in fluid communication with the sump 150. Additionally, the drain pump assembly 174 is in fluid communication with an external drain 173 to discharge used wash liquid. Further, the circulation pump assembly 172 is in fluid communication with lower spray arm assembly 144 and conduit 154 which extends to a back wall 156 of wash chamber 106, and upward along the back wall 156 for feeding wash liquid to the mid-level spray arm assembly 148 (FIG. 1) and the upper spray arm assembly. This configuration also applies to a drawer-type of dishwasher, as mentioned above.

As wash liquid is pumped through the lower spray arm assembly 144, and further delivered to the mid-level spray arm assembly 148 and the upper spray arm assembly (not shown), washing sprays are generated in the wash chamber 106, and wash liquid collects in the sump 150. The sump 150 may include a cover to prevent larger objects from entering the sump 150, such as a piece of silverware or another dishwasher item that is dropped beneath lower rack 132. A coarse filter and a fine filter (not shown) may be located adjacent the sump 150 to filter wash liquid for sediment and particles of predetermined sizes before flowing into the sump 150. Furthermore, a turbidity sensor 250 may be coupled to the sump 150 and used to sense a level of sediment in the sump 150 and to initiate a sump purge cycle where the contents or a fractional volume of the contents of the sump 150 are discharged when a turbidity level in the sump 150 approaches a predetermined threshold. Thus, an amount of used by the consumer appliance may be controlled in part by outputs of a turbidity sensor to more efficiently and effectively manage and reduce water use to only that needed, thereby reducing waste and cost. The sump 150 is filled with water through an inlet port 175 which outlets into wash chamber 106, as described in greater detail below.

As shown, a drain valve 186 is established in flow communication with the sump 150 and opens or closes flow communication between the sump 150 and a drain pump inlet 188. The drain pump assembly 174 is in flow communication with the drain pump inlet 188 and may include an electric motor for pumping fluid at the inlet 188 to an external drain system via drain 173. In one embodiment, when the drain pump is energized, a negative pressure is created in the drain pump inlet 188 and the drain valve 186 is opened, allowing fluid in the sump 150 to flow into the drain pump inlet 188 and be discharged from fluid circulation assembly 170 via the external drain 173. Alternatively, pump assemblies 172 and 174 may be connected directly to the side or the bottom of sump 150, and the pump assemblies may each include their own valving replacing drain valve 186. Other fluid circulation systems are possible as well, drawings fluid from sump 150 and providing as desired within wash chamber 106 or draining out of dishwasher 100. A selector valve 190 may be provided to select whether the upper arm 148, lower arm 144, or both receive fluid during circulation.

Referring to FIG. 2, a water supply 200 may be configured with the inlet port 175 for supplying wash liquid to the wash chamber 106. The water supply 200 may provide hot water only, cold water only, or either selectively as desired. As depicted, water supply 200 has a hot water inlet 204 that receives hot water from an external source, such as a hot water heater and a cold water input 206 that receives cold water from an external source. It should be understood that the term "water supply" is used herein to encompass any manner or combination of valves, lines or tubing, housing, and the like, and may simply comprise a conventional hot or cold water connection.

Figure 3:
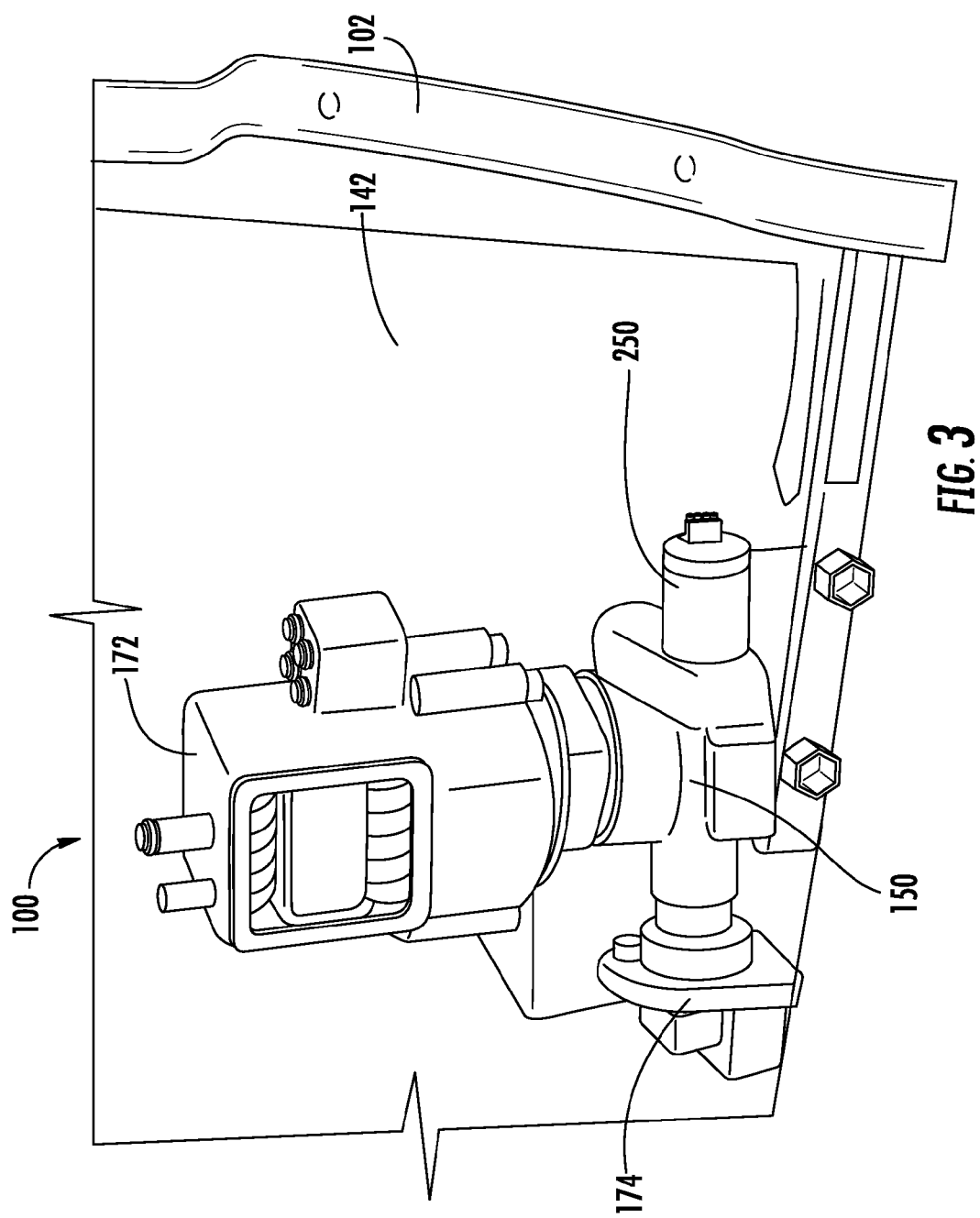
FIG. 3 provides a bottom view of a dishwasher showing the sump and one potential sensor location according to the present disclosure.

FIG. 3 shows a bottom area of dishwasher 100 including cabinet 102, sump 150, circulation pump assembly 172, and drain pump assembly 174. It should be understood that various other configurations are possible, including use with other types of consumer appliances or devices. Sensor 250 is provided for measuring a turbidity of a liquid within cabinet 102. As shown, sensor 250 is located in a side region of sump 150, but it could also be located other places in cabinet 102 where exposed to liquid.

As shown in FIGS. 4-6, sensor 250 includes a housing 252 having a first side 254 defining a channel 256 for holding the liquid and a second side 258 opposite the first side. Thus, channel 256 extends into sump 150 so that liquid within the sump flows through the channel and so that the second side 258 of the housing remains dry, sealed from the sump.

A first turbidity sensor 264 is located on an insert element 266 that is mountable to housing 252 on second side 258. Insert element 266 may comprise a printed circuit board or simply a holder. Insert element 266 has a slot 268 between two arms 270 sized to allow insert element to be slid into housing 252 so that the ends of the arms are on the opposite side of channel 256. It should be understood that various configurations are possible for housing 252 and insert 266 besides that shown. For example, housing 252 and insert 266 could be a unitary piece or more than two pieces.

First turbidity sensor 264 includes an emitter 272 and a receiver 274, as illustrated, located at ends of arms 270 on second side 258 of the housing on opposite sides of channel 256 so that the liquid can be present between the emitter and the receiver. Electrical connections 276, 278 (shown only schematically) are provided for emitter 272 and receiver 274 to connect to controller 137 via sockets 280, 282 on flange 284 of insert 266. First turbidity sensor 264 outputs a signal from receiver 274 to controller 137.

Emitter 272 may be an LED, such an IR LED or other LED, and receiver 274 may be a photovoltaic cell such as a photoresistor, phototransistor, or the like. If desired, emitter 272 may be an EL-23G photodiode from Kodenshi Corp., and receiver 274 may be an ST-23G photo transistor from Kodenshi Corp. The output of receiver 274 may be a value in voltage or other measurement. Emitter 272 and receiver 274 should be spaced apart sufficiently that a reliable measurement may be obtained even when the liquid is quite turbid in normal operating conditions for the consumer appliance. If emitter 272 is infrared, the housing 252 material can be a semi-transparent plastic such as polypropylene (PPN 4160). If other frequencies are used needing more transmission than housing 252 allows, a more transmissive material could be used, and/or optional transmissive "windows" 260, 262 could be added. Electrical connections 276, 278 are also shown only schematically and may each be two wires, coaxial, or other multi connection wiring, etc., as a voltage is provided to emitter 272 and a voltage is received and transmitted by receiver 274.

A second turbidity sensor 286 is also provided having an emitter 288 and a receiver 290 substantially identical to that of first turbidity sensor 264. Emitter 288 and receiver 290 are also located on second side 258 of the housing 252. However, emitter 288 and receiver 290 are spaced from channel 256 so that air, and not the liquid, is present between the second emitter and the receiver. Electrical connections 292, 294 (again, shown only schematically) are provided for emitter 288 and receiver 290 to connect to controller 137 via sockets 296, 298 as above. Sockets 280, 282, 296, 298 can be coaxial, plug-in, tip and ring, etc., type connectors as desired to connect multiple wires per socket and to connect to the turbidity sensors 264, 286 in conventional fashion. Connection 300 between sockets 280, 282, 296, 298 may be a plurality of wires (per socket), a bus, etc. to connect the output of the turbidity sensors 264, 286 with controller 137. One skilled in the art can therefore readily determine how best to wire and connect the various components for a particular application.

Second turbidity sensor 286 outputs a signal via receiver 290 that is combinable with signal from first turbidity sensor 264 to determine the turbidity of the liquid without determining the temperature of the liquid. Such can be done by assuming the temperature of the air at second turbidity sensor 286 approximates that of the liquid in channel 256 or is related to it in a mathematical fashion.

Therefore, by combining, (subtracting, adding, or otherwise accounting for) a change in output from second turbidity sensor 286 with the output of first turbidity sensor 264, the resulting signal is indicative of the turbidity of the liquid. For simplicity, the voltages provided to emitters 272 and 288 should accordingly be substantially identical. The temperature effects on the output are essentially canceled out by such process without need for determining the actual temperature as with some devices. Also, effects of aging of the housing, color change, voltage supply variation, etc., can all be accounted for by combining outputs of receivers 274 and 290.

Such avoids use of lookup tables, direct temperature measurements and the like. Such also avoids issues that may occur during lifespan of the product or during cycling if output of the first turbidity sensor should change over time. Assuming the second turbidity sensor is substantially similar, then both turbidity sensors should experience the same lifetime or cyclic changes, again canceling out such effects without having to directly measure them, and without throwing off a table of values, correction value calculation, etc., that may not be reliable for a changed sensor output over time. No stored values or tables are required, and if a sensor unit is changed out after installation, the self-correcting nature of the device should allow a replacement device to function immediately without resetting any table or the like, even if the turbidity sensors are slightly different from the original sensors, as long as the new devices operate together as above.

Accordingly, the present device provides a simple an reliable sensor and a consumer appliance wherein variations in turbidity readings caused by temperature changes or other changes can be corrected automatically, without ever having to measure temperature directly or consult a temperature based table or provide an empirical temperature based conversion factor, correction value, etc. It should be understood that various modifications are possible. Thus, the types of sensor, locations and arrangements can be changed. The manner in which they are attached together and attached to the housing, sump, and cabinet, exposed to the liquid and each other, etc. are also variable. In a broad sense, the disclosure is related to using two similar sensors, located close enough to each other that the temperature of each is approximately identical, and using a difference in their outputs to eliminate temperature related, voltage changes, changes in clarity of the housing, etc., effects from the output.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A sensor for measuring a turbidity of a liquid comprising:
   a housing having a first side along an exterior surface defining a channel for holding the liquid, the housing also having a second side along an interior surface;
   a first turbidity sensor having an emitter and a receiver, the emitter and receiver being located on the second side of the housing adjacent the channel so that the liquid can be present between the emitter and the receiver of the first turbidity sensor, the first turbidity sensor outputting a signal; and
   a second turbidity sensor having an emitter and a receiver, both the emitter and the receiver of the second turbidity sensor being separate from and substantially identical to that of the first turbidity sensor, the emitter and receiver being located on the second side of the housing spaced from the channel, the housing configured with the emitter and the receiver of the second turbidity sensor so that the liquid is precluded from passing between the emitter and the receiver of the second turbidity sensor at any time and so that air is located between the emitter and the receiver of the second turbidity sensor at all times, the second turbidity sensor outputting a signal, the signal from the first turbidity sensor being combinable with the signal from the second turbidity sensor to determine the turbidity of the liquid while accounting for the temperature of the liquid without determining the temperature of the liquid.

2. The sensor of claim 1, wherein the signals output by the first and second turbidity sensors vary according to the temperature of the liquid in the channel and the temperature of the air between the emitter and receiver of the second turbidity sensor.

3. The sensor of claim 1, wherein the emitters of the first and second turbidity sensors are LED's.

4. The sensor of claim 3, wherein the receivers of the first and second turbidity sensors are photovoltaic cells.

5. The sensor of claim 1, further including a controller, the controller including a memory, a microprocessor, and programming, the programming capable of calculating the turbidity of the liquid by combining the signal from the second turbidity sensor with the signal of the first turbidity sensor to substantially eliminate variations in signal from the first turbidity sensor caused by temperature change.

6. A consumer appliance for washing objects comprising:
   a cabinet holding wash elements that transition through a wash cycle to wash the objects; a liquid flow path through the cabinet used for washing the objects, the flow path defined in part by a housing having a first side along an exterior surface defining a channel for holding the liquid, the housing also having a second side along an interior surface;
   a controller in the cabinet for controlling the water cycle and the wash elements; and
   a sensor in the cabinet for measuring a turbidity of the liquid, the sensor including:
   a first turbidity sensor having an emitter and a receiver, the emitter and receiver being located on the second side of the housing adjacent the channel so that the liquid can be present between the emitter and the receiver of the first turbidity sensor, the first turbidity sensor outputting a signal to the controller; and
   a second turbidity sensor having an emitter and a receiver, both the emitter and the receiver of the second turbidity sensor being separate from and substantially identical to that of the first turbidity sensor, the emitter and receiver being located on the second side of the housing spaced from the channel, the housing configured with the emitter and the receiver of the second turbidity sensor so that the liquid is precluded from passing between the emitter and the receiver of the second turbidity sensor at any time and so that air is located between the emitter and the receiver of the second turbidity sensor at all times, the second turbidity sensor outputting a signal to the controller, the signal from the first turbidity sensor being combinable with the signal from the second turbidity sensor by the controller to determine the turbidity of the liquid while accounting for the temperature of the liquid without determining the temperature of the liquid.

7. The consumer appliance of claim 6, wherein the signals output by the first and second turbidity sensors vary according to the temperature of the liquid in the channel and the temperature of the air between the emitter and receiver of the second turbidity sensor.

8. The consumer appliance of claim 6, wherein the emitters of the first and second turbidity sensors are LED's.

9. The consumer appliance of claim 8, wherein the receivers of the first and second turbidity sensors are photovoltaic cells.

10. The consumer appliance of claim 6, wherein the controller includes a memory, a microprocessor, and programming, the programming capable of calculating the turbidity of the liquid by combining the signal from the second turbidity sensor with the signal of the first turbidity sensor to substantially eliminate variations in signal from the first turbidity sensor caused by temperature change.

* * * * *